United States Patent
Lee

(10) Patent No.: US 9,076,063 B2
(45) Date of Patent: Jul. 7, 2015

(54) METHOD AND APPARATUS FOR OBTAINING SYMMETRY INFORMATION OF OBJECTS

(71) Applicant: Samsung Medison Co., Ltd., Gangwon-do (KR)

(72) Inventor: Kwang-hee Lee, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 187 days.

(21) Appl. No.: 13/759,936

(22) Filed: Feb. 5, 2013

(65) Prior Publication Data

US 2013/0202174 A1    Aug. 8, 2013

(30) Foreign Application Priority Data

Feb. 6, 2012  (KR) .......................... 10-2012-0011795

(51) Int. Cl.
| | |
|---|---|
| G06K 9/00 | (2006.01) |
| G06K 9/46 | (2006.01) |
| A61B 8/08 | (2006.01) |
| G06T 7/60 | (2006.01) |
| A61B 8/00 | (2006.01) |

(52) U.S. Cl.
CPC ................ *G06K 9/46* (2013.01); *A61B 8/5223* (2013.01); *G06K 9/4633* (2013.01); *G06T 7/608* (2013.01); *G06T 2207/10132* (2013.01); *G06T 2207/30004* (2013.01)

(58) Field of Classification Search
USPC ......... 382/100, 103, 105, 128–134, 162, 168, 382/173, 181, 189–195, 203, 209, 232, 254, 382/274, 276, 286–296, 305, 312; 600/439, 600/443; 378/4, 21
See application file for complete search history.

(56) References Cited

U.S. PATENT DOCUMENTS

| | | | | |
|---|---|---|---|---|
| 5,889,892 | A | * | 3/1999 | Saito .............................. 382/293 |
| 5,966,472 | A | | 10/1999 | Kataoka et al. |
| 7,724,931 | B2 | * | 5/2010 | Kuth et al. .................... 382/128 |

(Continued)

FOREIGN PATENT DOCUMENTS

| | | |
|---|---|---|
| JP | 09-319880 A | 12/1997 |
| JP | 2004-160171 A | 6/2004 |

(Continued)

OTHER PUBLICATIONS

Extended European Search Report issued in European Patent Application 13153866.2 dated Jun. 3, 2013.

(Continued)

*Primary Examiner* — Seyed Azarian
(74) *Attorney, Agent, or Firm* — McDermott Will & Emery LLP

(57) ABSTRACT

A method of obtaining symmetry information of objects, the method includes: acquiring at least one second feature point matched to at least one first feature point of the objects, which are extracted from an ultrasound image of the objects, from a mirror image obtained by reversing the ultrasound image based on an arbitrary axis; acquiring a third feature point corresponding to a location of the second feature point in the mirror image from the ultrasound image; determining a symmetry axis of the objects by using a center point between the first feature point and the third feature point; and acquiring symmetry information indicating whether the objects are symmetrical about the determined symmetry axis.

18 Claims, 6 Drawing Sheets

(56) References Cited

U.S. PATENT DOCUMENTS

| | | | |
|---|---|---|---|
| 8,675,939 B2* | 3/2014 | Moctezuma de la Barrera | 382/131 |
| 2011/0071395 A1* | 3/2011 | Miller et al. | 600/439 |
| 2011/0224546 A1* | 9/2011 | Lee et al. | 600/443 |
| 2011/0295120 A1* | 12/2011 | Lee | 600/443 |

FOREIGN PATENT DOCUMENTS

| | | |
|---|---|---|
| JP | 2007-022239 A | 2/2007 |
| JP | 2007-104551 A | 4/2007 |
| JP | 2007-130462 A | 5/2007 |
| KR | 10-2011-0057749 A | 6/2011 |

OTHER PUBLICATIONS

Shih-Kuan Liao et al., "Segmentation of Natural Image Based on Symmetry Features," Proceedings from the 2009 Fourth International Conference on Innovative Computing, Information and Control, pp. 523-527, Dec. 7, 2009.

Korean Notice of Allowance issued in Korean Application No. KR10-2012-0011795 dated Jul. 1, 2014, with English translation.

\* cited by examiner

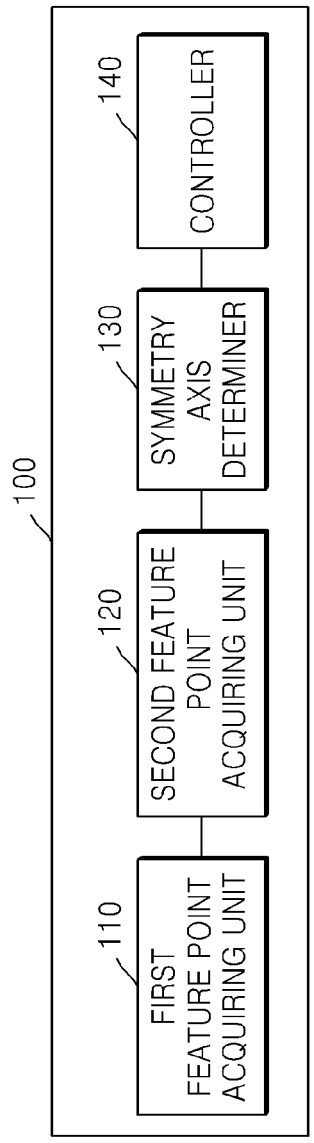
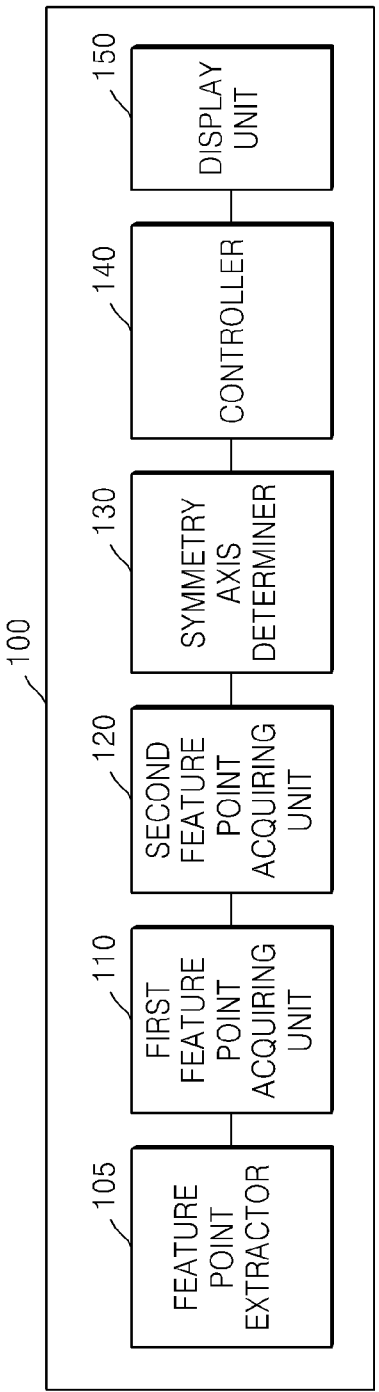

FIG. 2A
FIG. 2B
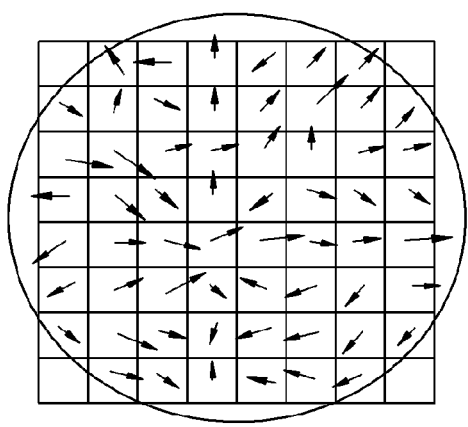
IMAGE GRADIENTS
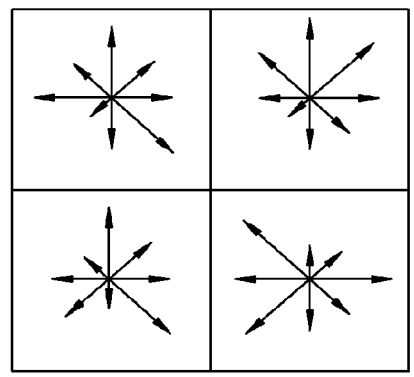
KEYPOINT DESCRIPTOR (b)

METHOD AND APPARATUS FOR OBTAINING SYMMETRY INFORMATION OF OBJECTS

CROSS-REFERENCE TO RELATED PATENT APPLICATION

This application claims the benefit of Korean Patent Application No. 10-2012-0011795, filed on Feb. 6, 2012, in the Korean Intellectual Property Office, the disclosure of which is incorporated herein in its entirety by reference.

BACKGROUND OF THE INVENTION

1. Field of the Invention

The present invention relates to a method and apparatus for obtaining symmetry information of objects, and more particularly, to a method and apparatus for determining a symmetry axis of objects by using an ultrasound image of the objects and obtaining symmetry information of the objects.

2. Description of the Related Art

Ultrasound devices are mandatory to observe a structure inside an organism. Such an ultrasound device is a noninvasive diagnostic device that displays structural details, internal tissues, and a fluid flow of a human body.

Such an ultrasound device transmits an ultrasound signal to an object through a human body and receives an echo signal reflected from the object, thereby displaying an image of a structure inside the human body.

Objects, such as the brain, lungs, and kidneys, forming symmetry about a certain symmetry axis exist inside a human body. In a medical examination, determination on whether areas of objects divided based on a symmetry axis are symmetrical is important. Thus, an efficient method of determining whether objects are symmetrical is required.

SUMMARY OF THE INVENTION

The present invention provides a method and apparatus for obtaining symmetry information of objects, whereby a symmetry axis of the objects is determined from an ultrasound image of the objects, and symmetry information indicating whether the objects are symmetrical about the determined symmetry axis is obtained.

According to an aspect of the present invention, there is provided a method of obtaining symmetry information of objects, the method including: acquiring at least one second feature point matched to at least one first feature point of the objects, which are extracted from an ultrasound image of the objects, from a mirror image obtained by reversing the ultrasound image based on an arbitrary axis; acquiring a third feature point corresponding to a location of the second feature point in the mirror image from the ultrasound image; determining a symmetry axis of the objects by using a center point between the first feature point and the third feature point; and acquiring symmetry information indicating whether the objects are symmetrical about the determined symmetry axis.

The acquiring of the at least one second feature point may include acquiring the at least one second feature point having second orientation information corresponding to first orientation information of the at least one first feature point.

The acquiring of the symmetry information may include acquiring the symmetry information by using at least one of brightness, an edge shape, and a gradient of each first and second area divided based on the symmetry axis of the objects.

The method may further include displaying an asymmetrical part of the first and second areas based on the acquired symmetry information.

The method may further include extracting the at least one first feature point from the ultrasound image and the at least one second feature point from the mirror image by using at least one of a block matching algorithm, a Scale Invariant Feature Transform (SIFT), and Speeded-Up Robust Features (SURF).

The determining of the symmetry axis of the objects may include determining the symmetry axis of the objects by using at least one of a Random Sample Consensus (RANSAC), a Hough transform, a BIG-M method, and a least squares method.

According to another aspect of the present invention, there is provided a method of obtaining symmetry information of objects, the method including: acquiring second orientation information by reversing first orientation information of a first feature point among feature points of the objects, which are extracted from an ultrasound image of the objects, based on an arbitrary axis; acquiring a second feature point having orientation information corresponding to the second orientation information from among the feature points; determining a symmetry axis of the objects by using a center point between the first feature point and the second feature point; and acquiring symmetry information indicating whether the objects are symmetrical about the determined symmetry axis.

The first orientation information and the second orientation information may include an orientation histogram.

According to another aspect of the present invention, there is provided an apparatus for obtaining symmetry information of objects, the apparatus including: a first feature point acquiring unit for acquiring at least one second feature point matched to at least one first feature point of the objects, which are extracted from an ultrasound image of the objects, from a mirror image obtained by reversing the ultrasound image based on an arbitrary axis; a second feature point acquiring unit for acquiring a third feature point corresponding to a location of the second feature point in the mirror image from the ultrasound image; a symmetry axis determiner for determining a symmetry axis of the objects by using a center point between the first feature point and the third feature point; and a controller for acquiring symmetry information indicating whether the objects are symmetrical about the determined symmetry axis.

The first feature point acquiring unit may acquire the at least one second feature point having second orientation information corresponding to first orientation information of the at least one first feature point.

The controller may acquire the symmetry information by using at least one of brightness, an edge shape, and a gradient of each first and second area divided based on the symmetry axis of the objects.

The apparatus may further include a display unit for displaying an asymmetrical part of the first and second areas based on the acquired symmetry information.

The apparatus may further include a feature point extractor for extracting the at least one first feature point from the ultrasound image and the at least one second feature point from the mirror image by using at least one of a block matching algorithm, a Scale Invariant Feature Transform (SIFT), and Speeded-Up Robust Features (SURF).

The symmetry axis determiner may determine the symmetry axis of the objects by using at least one of a Random Sample Consensus (RANSAC), a Hough transform, a BIG-M method, and a least squares method.

According to another aspect of the present invention, there is provided an apparatus for obtaining symmetry information of objects, the apparatus including: a controller for acquiring second orientation information by reversing first orientation information of a first feature point among feature points of the objects, which are extracted from an ultrasound image of the objects, based on an arbitrary axis; a feature point acquiring unit for acquiring a second feature point having orientation information corresponding to the second orientation information from among the feature points; and a symmetry axis determiner for determining a symmetry axis of the objects by using a center point between the first feature point and the second feature point, wherein the controller acquires symmetry information indicating whether the objects are symmetrical about the determined symmetry axis.

The first orientation information and the second orientation information may include an orientation histogram.

A computer-readable program for executing the method of obtaining symmetry information of objects may be recorded in a computer-readable recording medium.

The apparatus for obtaining symmetry information of objects may be included in an ultrasound apparatus.

BRIEF DESCRIPTION OF THE DRAWINGS

The above and other feature points and advantages of the present invention will become more apparent by describing in detail exemplary embodiments thereof with reference to the attached drawings in which:

FIG. 1A is a block diagram of an apparatus for obtaining symmetry information of objects, according to an embodiment of the present invention;

FIG. 1B is a block diagram of an apparatus for obtaining symmetry information of objects, according to another embodiment of the present invention;

FIGS. 2A and 2B are diagrams for describing a method of acquiring orientation information of feature points extracted from an ultrasound image based on a Scale Invariant Feature Transform (SIFT);

DETAILED DESCRIPTION OF THE INVENTION

Figure 3A:
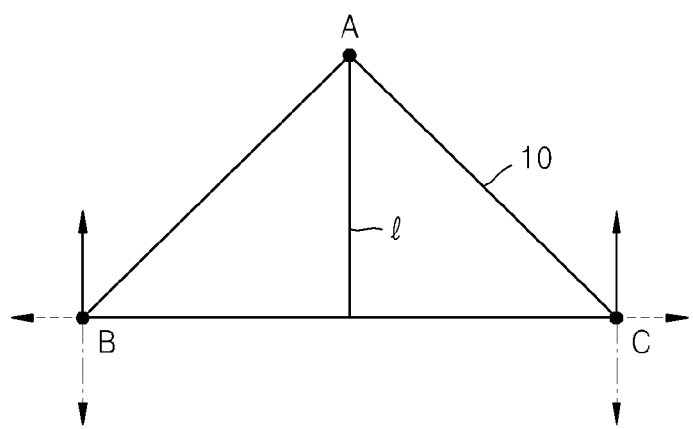
FIGS. 3A and 3B are diagrams for describing a method of determining a symmetry axis of objects in the apparatus for obtaining symmetry information of objects, according to an embodiment of the present invention.

The merits and characteristics of the present invention and methods for achieving them will be clear with reference to the embodiments described below in detail with the attached drawings. However, the present invention is not limited to the embodiments disclosed below, and the present invention will be implemented in various forms; rather, these embodiments are provided so that this disclosure will be thorough and complete, and will fully convey the concept of the invention to those of ordinary skill in the art. The present invention is only defined by the following claims. Like reference numbers are used to refer to like elements throughout the specification.

The term 'unit' used in the embodiments indicates a software or hardware component, such as a Field Programmable Gate Array (FPGA) or Application Specific Integrated Circuit (ASIC), and performs a certain role. However, the term 'unit' is not limited to software or hardware. The term 'unit' may be configured to be in an addressable storage medium or to reproduce one or more processors. Thus, for example, the term 'unit' includes components, such as software components, object-oriented software components, class components, and task components, processors, functions, attributes, procedures, sub-routines, program code segments, drivers, firmware, micro-codes, circuits, data, databases, data structures, tables, arrays, and variables. A function provided in components and 'units' may be performed by combining a smaller number of components and 'units' or further separating additional components and 'units' therefrom.

Expressions such as "at least one of," when preceding a list of elements, modify the entire list of elements and do not modify the individual elements of the list.

FIG. 1A is a block diagram of an apparatus 100 for obtaining symmetry information of objects, according to an embodiment of the present invention.

Referring to FIG. 1A, the apparatus 100 according to an embodiment of the present invention may include a first feature point acquiring unit 110, a second feature point acquiring unit 120, a symmetry axis determiner 130, and a controller 140. Referring to FIG. 1B, the apparatus 100 according to another embodiment of the present invention may include a feature point extractor 105 and a display unit 150 in addition to the first feature point acquiring unit 110, the second feature point acquiring unit 120, the symmetry axis determiner 130, and the controller 140.

The apparatus 100 may be included in an ultrasound apparatus, and each of the feature point extractor 105, the first feature point acquiring unit 110, the second feature point acquiring unit 120, the symmetry axis determiner 130, and the controller 140 may be implemented by a micro chip. Although the first feature point acquiring unit 110 and the second feature point acquiring unit 120 are separated in FIGS. 1A and 1B, the first feature point acquiring unit 110 and the second feature point acquiring unit 120 may be formed as a single feature point acquiring unit.

The feature point extractor 105 extracts feature points indicating characteristics of objects from an ultrasound image of the objects. The extraction of feature points indicates a process of repeatedly extracting points at the same locations even though various transforms are performed on an image. In the image processing field, the extraction of feature points from an image is popularly used for techniques, such as object recognition and fingerprint recognition.

The feature point extractor 105 may extract feature points from a specific image by using any one of a block matching algorithm, a Scale Invariant Feature Transform (SIFT), and Speeded-Up Robust Features (SURF).

The block matching algorithm is a method of dividing an image into blocks having a predetermined size and representing all pixels in each block as a single motion vector.

The SIFT is an algorithm of extracting feature points not changed regardless of a size or rotation of an image and matching the extracted feature points with feature points extracted from another image.

The SURF is also an algorithm of extracting feature points from an image and matching the extracted feature points with feature points extracted from another image, like the SIFT. However, a matching speed of the SURF is faster than that of the SIFT.

The feature point extractor 105 extracts a first feature point of the objects from an ultrasound image of the objects. In addition, the feature point extractor 105 extracts a second feature point from a mirror image obtained by reversing the ultrasound image based on an arbitrary axis. Each of the number of extracted first feature points and the number of extracted second feature points may be plural.

The first feature point acquiring unit 110 acquires a second feature point matched to the first feature point. The controller 140 acquires orientation information of the first feature point and the second feature point, and the first feature point acquiring unit 110 may acquire the second feature point matched to the first feature point based on the acquired orientation information. The number of second feature points matched to the first feature point may be plural, and in this case, the first feature point acquiring unit 110 determines a single second feature point by using distance information between the feature points. The orientation information will be described in detail below with reference to FIGS. 2A and 2B.

The second feature point acquiring unit 120 acquires a third feature point corresponding to a location of the second feature point in the mirror image from the ultrasound image.

When the ultrasound image is reversed, orientation information of feature points included in the feature points is also reversed. Thus, a location of the first feature point in the ultrasound image and a location of the second feature point in the mirror image do not correspond to each other in the same image. If the third feature point corresponding to the location of the second feature point is acquired from the ultrasound image, the first feature point and the third feature point correspond to feature points symmetrical to each other about a symmetry axis. This will be described below in detail with reference to FIGS. 3A and 3B and FIGS. 4A and 4B.

The symmetry axis determiner 130 determines a symmetry axis of the objects by using a center point between the first feature point in the ultrasound image and the acquired third feature point. If a plurality of first feature points match with a plurality of second feature points, the number of center points between the first feature points and acquired third feature points may be plural, and in this case, the symmetry axis of the objects may be determined by connecting the center points.

If a third feature point that is not matched to the first feature point is acquired, a center point between the first feature point and the acquired third feature point corresponds to data that is separate from the symmetry axis to be actually determined. That is, outlier data that is separate from a data distribution of acquired center points must be excluded from inlier data. To do this, the symmetry axis determiner 130 determines the symmetry axis of the objects by using at least one of a Random Sample Consensus (RANSAC), a Hough transform, a BIG-M method, and a least squares method. According to these methods, a constant mathematical model is acquired by removing outlier data from among a plurality of center points.

The controller 140 acquires symmetry information indicating whether the objects are symmetrical about the determined symmetry axis. In detail, the symmetry information of the objects is acquired by using at least one of brightness, an edge shape, and a gradient of each first and second area of the objects divided based on the symmetry axis of the objects.

The display unit 150 displays an asymmetrical part of the first and second areas based on the symmetry information acquired by the controller 140.

FIGS. 2A and 2B are diagrams for describing a method of acquiring orientation information of feature points extracted from an ultrasound image based on the SIFT.

The SIFT extracts feature points from an image and generates a feature descriptor of the extracted feature points, and orientation information may be included in the feature descriptor.

First, the feature point extractor 105 extracts a pixel satisfying a predetermined criterion from an image as a feature point. The controller 140 generates a feature descriptor of the extracted feature point.

The controller 140 generates a feature descriptor including location, size, and azimuth information with respect to surrounding pixels based on the extracted feature point. In detail, the controller 140 generates orientation information including one or more orientation histograms based on image gradients with respect to surrounding pixels about a finally selected feature point. A feature descriptor is generated as a 128-dimensional vector by storing parameters, such as image coordinates and a Gaussian scale of the feature point, in the orientation information.

FIG. 2A shows an example of gradient values of surrounding pixels in an image from which a feature point is extracted, and FIG. 2B shows orientation histograms acquired using the gradient values. A direction and length of each of arrows indicate a direction and magnitude of a corresponding gradient, respectively.

The controller 140 may acquire reversed orientation information by reversing the generated orientation information based on an arbitrary axis.

Figure 3B:
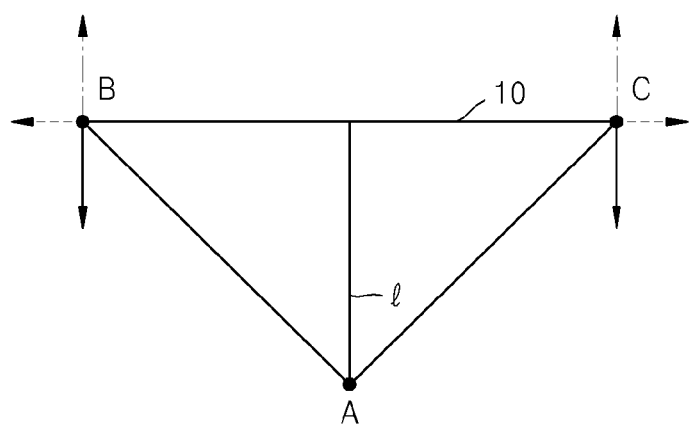

FIGS. 3A and 3B are diagrams for describing a method of determining a symmetry axis of objects in the apparatus 100 for obtaining symmetry information of objects, according to an embodiment of the present invention.

First, first feature points A, B, and C are extracted from an ultrasound image of objects 10, which is shown in FIG. 3A. Then, second feature points A, B, and C are extracted from a mirror image of the ultrasound image, which is shown in FIG. 3B. The mirror image shown in FIG. 3B is generated by reversing the ultrasound image shown in FIG. 3A based on an axis connecting the feature points B and C. Arrows shown at the feature points B and C indicate orientation information at the feature points B and C, respectively. Assuming that I denotes a symmetry axis of the objects 10, the feature point C must be acquired as a feature point symmetrical to the feature point B of FIG. 3A.

When the feature points A, B, and C in the ultrasound image shown in FIG. 3A are matched with the feature points A, B, and C in the mirror image shown in FIG. 3B, the feature point B of FIG. 3A will be matched with the feature point C of FIG. 3B because orientation information of the feature point B of FIG. 3A rotated clockwise by 180° corresponds to orientation information of the feature point C of FIG. 3B. In the ultrasound image, a feature point corresponding to the feature point C of FIG. 3B is the feature point C of FIG. 3A, and the symmetry axis I may be determined using a center point between the feature points B and C of FIG. 3A.

Figure 4A:
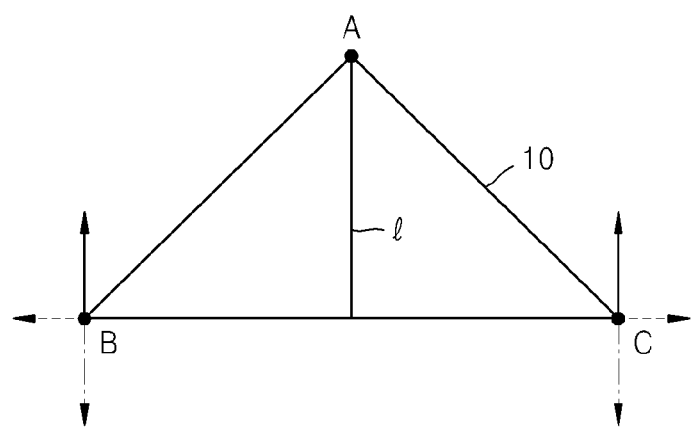
FIGS. 4A and 4B are diagrams for describing a method of determining a symmetry axis of objects in the apparatus for obtaining symmetry information of objects, according to another embodiment of the present invention.
Figure 4B:
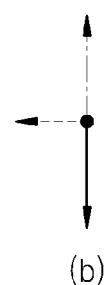

FIGS. 4A and 4B are diagrams for describing a method of determining a symmetry axis of objects in the apparatus 100 for obtaining symmetry information of objects, according to another embodiment of the present invention.

Feature points B and C are extracted from an ultrasound image shown in FIG. 4A. Arrows shown at the feature points B and C indicate orientation information at the feature points B and C, respectively. When orientation information of the feature point B is reversed based on an axis connecting the feature points B and C, orientation information shown in FIG. 4B is acquired. When a feature point having orientation information corresponding to the acquired orientation information is searched for, the feature point C shown in FIG. 4A is extracted. A symmetry axis I may be determined using a center point between the feature points B and C.

Figure 5:
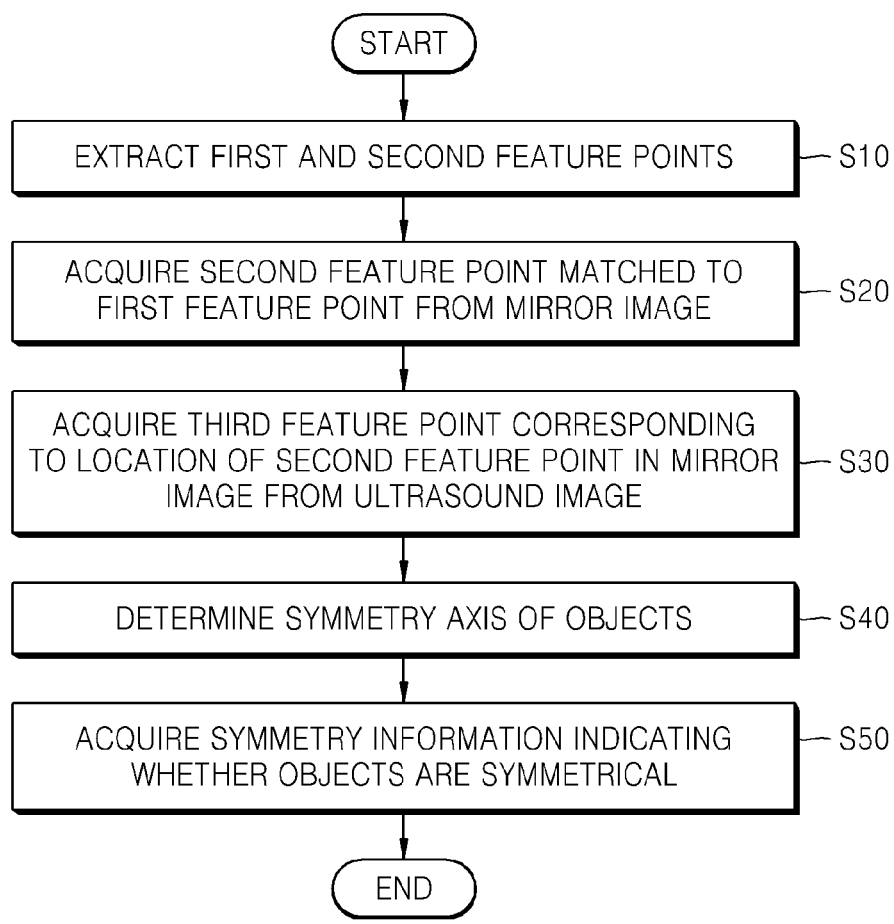
FIG. 5 is a flowchart illustrating a method of obtaining symmetry information of objects, according to an embodiment of the present invention.

FIG. 5 is a flowchart illustrating a method of obtaining symmetry information of objects, according to an embodiment of the present invention. Referring to FIG. 5, the method includes operations sequentially processed in the apparatus 100 shown in FIGS. 1A and 1B. Thus, although omitted hereinafter, the description of the apparatus 100 shown in FIGS. 1A and 1B also applies to the method of FIG. 5.

Referring to FIG. 5, in operation 510, the feature point extractor 105 extracts at least one first feature point from an ultrasound image of objects and extracts at least one second feature point from a mirror image. The feature point extractor 105 may extract feature points using at least one of the block matching algorithm, the SIFT, and the SURF.

In operation S20, the first feature point acquiring unit 110 acquires a second feature point matched to the first feature point from the mirror image. Whether the second feature point is matched to the first feature point may be determined using orientation information of the first feature point and the second feature point.

In operation S30, the controller 140 acquires a third feature point corresponding to a location of the second feature point in the mirror image from the ultrasound image. The third feature point is symmetrical to the first feature point.

In operation S40, the symmetry axis determiner 130 determines a symmetry axis of the objects by using a center point between the first feature point and the third feature point. The symmetry axis determiner 130 determines the symmetry axis of the objects by using at least one of the RANSAC, the Hough transform, the BIG-M method, and the least squares method to exclude outlier data that is separate from an acquired center point data distribution from inlier data.

In operation S50, the controller 140 acquires symmetry information indicating whether the objects are symmetrical about the determined symmetry axis. The symmetry information may be acquired by comparing any one of brightness, an edge shape, and a gradient of one of the areas of the objects, which are divided based on the symmetry axis, with a corresponding one of the other area.

Figure 6:
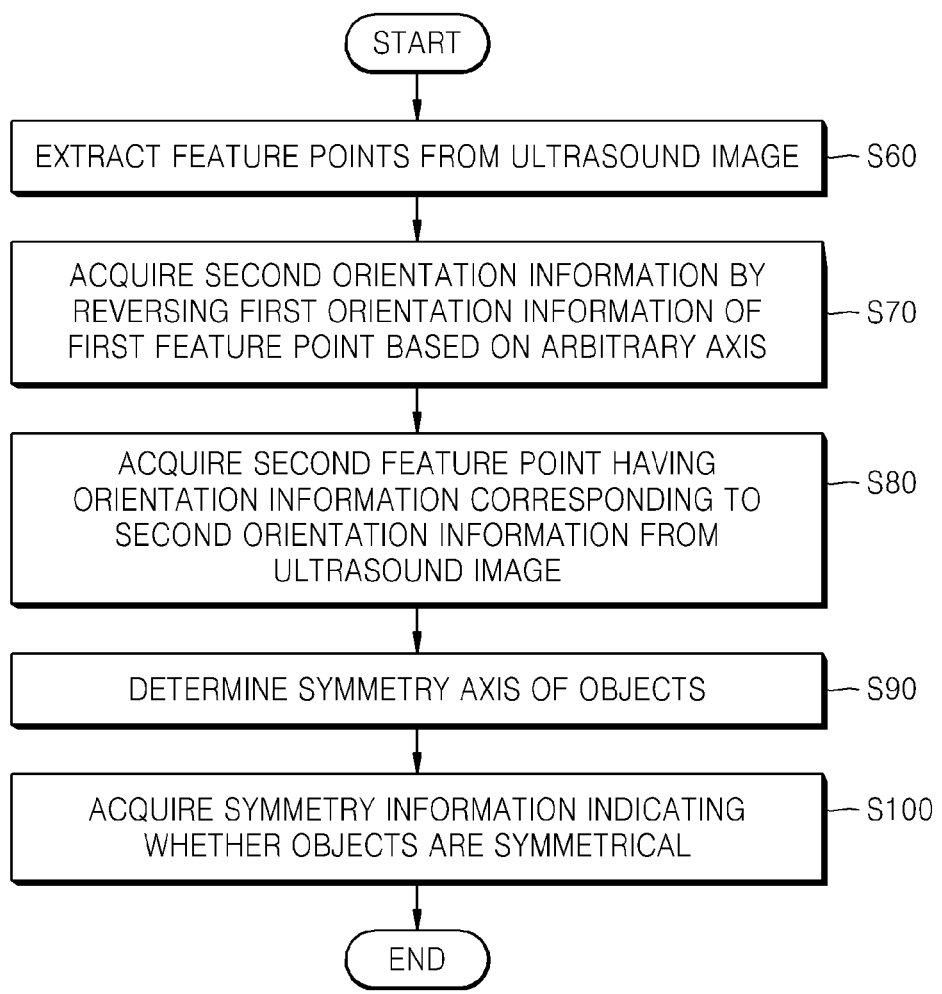
FIG. 6 is a flowchart illustrating a method of obtaining symmetry information of objects, according to another embodiment of the present invention.

FIG. 6 is a flowchart illustrating a method of obtaining symmetry information of objects, according to another embodiment of the present invention.

Referring to FIG. 6, in operation S60, the feature point extractor 105 extracts feature points from an ultrasound image of objects.

In operation S70, the controller 140 acquires second orientation information by reversing first orientation information of a first feature point among the extracted feature points based on an arbitrary axis.

In operation S80, a feature point acquiring unit acquires a second feature point having orientation information corresponding to the acquired second orientation information from among the extracted feature points. The second feature point is symmetrical to the first feature point.

In operation S90, the symmetry axis determiner 130 determines a symmetry axis of the objects by using a center point between the first feature point and the second feature point.

In operation S100, the controller 140 acquires symmetry information indicating whether the objects are symmetrical about the determined symmetry axis.

According to the embodiments of the present invention, a symmetry axis of objects may be determined from an ultrasound image of the objects, and symmetry information indicating whether the objects are symmetrical about the determined symmetry axis may be acquired.

The embodiments of the present invention can be written as computer programs and can be implemented in general-use digital computers that execute the programs using a computer-readable recording medium. Examples of the computer-readable recording medium include storage media such as magnetic storage media (e.g., ROM, floppy disks, hard disks, etc.), optical recording media (e.g., CD-ROMs, or DVDs), etc.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of obtaining symmetry information of objects, the method comprising:
    obtaining an ultrasound image of the objects, the ultrasound image containing at least one first feature point;
    acquiring at least one second feature point in a mirror image obtained by reversing the ultrasound image based on an arbitrary axis, the at least one second feature point in the mirror image matching the at least one first feature point in the ultrasound image under a predetermined algorithm;
    acquiring a third feature point in the ultrasound image, the third feature point corresponding to a location of the second feature point in the mirror image;
    determining a symmetry axis of the objects by using a center point between the first feature point and the third feature point; and
    acquiring symmetry information indicating whether the objects are symmetrical about the determined symmetry axis.

2. The method of claim 1, wherein the acquiring the at least one second feature point comprises acquiring the at least one second feature point having second orientation information corresponding to first orientation information of the at least one first feature point.

3. The method of claim 1, wherein the acquiring the symmetry information comprises acquiring the symmetry information by using at least one of brightness, an edge shape, and a gradient of each first and second area divided based on the symmetry axis of the objects.

4. The method of claim 3, further comprising displaying an asymmetrical part of the first and second areas based on the acquired symmetry information.

5. The method of claim 1, further comprising extracting the at least one first feature point from the ultrasound image and the at least one second feature point from the mirror image by using at least one of a block matching algorithm, a Scale Invariant Feature Transform (SIFT), and Speeded-Up Robust Features (SURF).

6. The method of claim 1, wherein the determining the symmetry axis of the objects comprises determining the symmetry axis of the objects by using at least one of a Random Sample Consensus (RANSAC), a Hough transform, a BIG-M method, and a least squares method.

7. A non-transitory computer-readable recording medium storing a computer-readable program for executing the method of claim 1.

8. A method of obtaining symmetry information of objects, the method comprising:
    obtaining an ultrasound image of the objects, the ultrasound image containing at least one first feature point;
    acquiring second orientation information by reversing, based on an arbitrary axis, first orientation information of the first feature point among feature points of the objects in the ultrasound image;

acquiring a second feature point having orientation information corresponding to the second orientation information from among the feature points;

determining a symmetry axis of the objects by using a center point between the first feature point and the second feature point; and acquiring symmetry information indicating whether the objects are symmetrical about the determined symmetry axis.

9. The method of claim 8, wherein the first orientation information and the second orientation information include an orientation histogram.

10. A non-transitory computer-readable recording medium storing a computer-readable program for executing the method of claim 8.

11. An apparatus for obtaining symmetry information of objects, the apparatus comprising:
a feature point acquiring unit for:
obtaining an ultrasound image of the objects, the ultrasound image containing at least one first feature point,
acquiring at least one second feature point in a mirror image obtained by reversing the ultrasound image based on an arbitrary axis, the at least one second feature point in the mirror image matching the at least one first feature point in the ultrasound image under a predetermined algorithm, and
acquiring a third feature point in the ultrasound image, the third feature point corresponding to a location of the second feature point in the mirror image;
a symmetry axis determiner for determining a symmetry axis of the objects by using a center point between the first feature point and the third feature point; and
a controller for acquiring symmetry information indicating whether the objects are symmetrical about the determined symmetry axis.

12. The apparatus of claim 11, wherein the first feature point acquiring unit acquires the at least one second feature point having second orientation information corresponding to first orientation information of the at least one first feature point.

13. The apparatus of claim 11, wherein he controller acquires the symmetry information by using at least one of brightness, an edge shape, and a gradient of each first and second area divided based on the symmetry axis of the objects.

14. The apparatus of claim 13, further comprising a display unit for displaying an asymmetrical part of the first and second areas based on the acquired symmetry information.

15. The apparatus of claim 11, further comprising a feature point extractor for extracting the at least one first feature point from the ultrasound image and the at least one second feature point from the mirror image by using at least one of a block matching algorithm, a Scale Invariant Feature Transform (SIFT), and Speeded-Up Robust Features (SURF).

16. The apparatus of claim 11, wherein the symmetry axis determiner determines the symmetry axis of the objects by using at least one of a Random Sample Consensus (RANSAC), a Hough transform, a BIG-M method, and a least squares method.

17. An apparatus for obtaining symmetry information of objects, the apparatus comprising:
a controller for:
obtaining an ultrasound image of the objects, the ultrasound image containing at least one first feature point, and
acquiring second orientation information by reversing, based on an arbitrary axis, first orientation information of the first feature point among feature points of the objects;
a feature point acquiring unit for acquiring a second feature point having orientation information corresponding to the second orientation information from among the feature points; and
a symmetry axis determiner for determining a symmetry axis of the objects by using a center point between the first feature point and the second feature point,
wherein the controller acquires symmetry information indicating whether the objects are symmetrical about the determined symmetry axis.

18. The apparatus of claim 17, wherein the first orientation information and the second orientation information include an orientation histogram.

* * * * *